(12) United States Patent
Umeda

(10) Patent No.: US 11,338,300 B2
(45) Date of Patent: May 24, 2022

(54) CELL WALL OR CELL MEMBRANE DISRUPTING DEVICE, AND METHOD OF USING THE SAME

(71) Applicant: NIKKAN TOKUSHU Co., Ltd., Shimonoseki (JP)

(72) Inventor: Kounichi Umeda, Shimonoseki (JP)

(73) Assignee: NIKKAN TOKUSHU Co., Ltd., Shimonoseki (JP)

( * ) Notice: Subject to any disclaimer, the term of this patent is extended or adjusted under 35 U.S.C. 154(b) by 190 days.

(21) Appl. No.: 16/304,392

(22) PCT Filed: Nov. 24, 2016

(86) PCT No.: PCT/JP2016/084844
§ 371 (c)(1),
(2) Date: Nov. 26, 2018

(87) PCT Pub. No.: WO2017/203732
PCT Pub. Date: Nov. 30, 2017

(65) Prior Publication Data
US 2019/0217307 A1    Jul. 18, 2019

(30) Foreign Application Priority Data
May 27, 2016 (JP) .................... PCT/JP2016/065808

(51) Int. Cl.
*B02C 19/18* (2006.01)
*C02F 11/04* (2006.01)
(Continued)

(52) U.S. Cl.
CPC ............... *B02C 19/18* (2013.01); *A23L 5/30* (2016.08); *B02C 7/02* (2013.01); *C02F 11/00* (2013.01);
(Continued)

(58) Field of Classification Search
CPC ..... B02C 19/18; B02C 13/18; B02C 13/1807; B02C 7/00; B02C 7/02; B02C 7/04;
(Continued)

(56) References Cited

U.S. PATENT DOCUMENTS 4,038,433 A * 7/1977 Manser ..................... B02B 3/14
426/615
4,684,072 A * 8/1987 Nelson .................... B02C 17/04
241/171

(Continued)

FOREIGN PATENT DOCUMENTS

CN          105105082 A  * 12/2015
CN          105105082 A    12/2015
(Continued)

OTHER PUBLICATIONS

International Search Report for PCT/JP2016/084844, dated Feb. 28, 2017.
(Continued)

*Primary Examiner* — Matthew Katcoff
(74) *Attorney, Agent, or Firm* — Merchant & Gould P.C.

(57) ABSTRACT

Provided is a cell wall or cell membrane disrupting device whereby cell walls and/or cell membranes of microorganisms, algae and the like contained in organic sludge and the like are disrupted, the device comprising a fixed disc, a rotating disc, a rotating shaft for driving of the rotating disc, a pressure reducing means and a housing, wherein at least one pair of the fixed disc and rotating disc are disposed facing each other, the center section of the fixed disc has a hollow section that is larger than the outer diameter of the rotating shaft passing through the center section, shearing force generated between the rotating disc and the fixed disc is applied to a target fluid having a water content of 89% or higher that has been loaded into the device, and the pressure inside the cell wall or cell membrane disrupting device is (Continued)

reduced to no greater than −0.08 MPa by the pressure reducing means. The device can contribute to increasing biogas, reducing sludge, culturing of algae, plant cultivation and culturing of marine products, and also to separation of $CH_4$ and $CO_2$, for example, as resources.

17 Claims, 11 Drawing Sheets

(51) Int. Cl.
    *C02F 11/00*     (2006.01)
    *C12M 1/33*     (2006.01)
    *B02C 7/02*     (2006.01)
    *A23L 5/30*     (2016.01)
    *C02F 11/12*     (2019.01)
    *C12N 1/06*     (2006.01)

(52) U.S. Cl.
    CPC .............. *C02F 11/04* (2013.01); *C02F 11/12* (2013.01); *C12M 1/33* (2013.01); *C12N 1/066* (2013.01); *A23V 2002/00* (2013.01); *Y02A 40/20* (2018.01); *Y02E 50/30* (2013.01); *Y02W 10/37* (2015.05); *Y02W 30/40* (2015.05)

(58) Field of Classification Search
    CPC .. B02C 7/06; B02C 7/08; B02C 17/16; B02C 17/163; B02C 17/165; B02C 17/166
    See application file for complete search history.

(56) References Cited

U.S. PATENT DOCUMENTS

| | | | | |
|---|---|---|---|---|
| 5,312,055 A | * | 5/1994 | Barthelmess | B02C 17/16 241/172 |
| 5,361,996 A | * | 11/1994 | Svensson | B02C 17/16 241/30 |
| 5,379,952 A | * | 1/1995 | Geiger | B02C 17/16 241/172 |
| 6,059,971 A | | 5/2000 | Vit et al. | |
| 2015/0175954 A1 | | 6/2015 | Kunita et al. | |

FOREIGN PATENT DOCUMENTS

| | | |
|---|---|---|
| EP | 2465610 A1 | 6/2012 |
| JP | S53-030004 A | 3/1978 |
| JP | H10-230247 A | 9/1998 |
| JP | 2000343098 A | 12/2000 |
| JP | 2002-282721 A | 10/2002 |
| JP | 2002-336898 A | 11/2002 |
| JP | 2006-000802 A | 1/2006 |
| JP | 3731204 B2 | 1/2006 |
| JP | 2006-334489 A | 12/2006 |
| JP | 2007-268515 A | 10/2007 |
| JP | 2011-234676 A | 11/2011 |
| JP | 2012-254426 A | 12/2012 |
| JP | 2013-133242 A | 7/2013 |
| KR | 10-0814405 B1 | 3/2008 |
| WO | 2013/176261 A1 | 11/2013 |

OTHER PUBLICATIONS

International Search Report for PCT/JP2016/065808, dated Jun. 21, 2016.
"Guidance on Comprehensive Biological Experiments", edited by Weian Xu, Suzhou University Press: 37 (2010).
"Sludge Drying and Incineration Technology", edited by Luochun Wang et al., Beijing: Metallurgical Industry Press: 2 (2010).
"Hydraulic and Pneumatic Technology", edited by Yihe Li et al., Beijing: National Defense of Industry Press: 271-272 (2006).
"Principle of Chemical Engineering", edited by Qin Zhong et al., 3rd Edition, Beijing: National Defense of Industry Press: 8-9 (2013).
"Hydraulic Pneumatic Technology Q and A", edited by Nengwu Zhang et al., Changsha: Hunan Science and Technology Press: 42 (2014).
"Fluid Mechanics and Hydraulic Transmission", edited by Minxun Lu et al., Shanghai: Tongji University Press: 47 (2006).

* cited by examiner

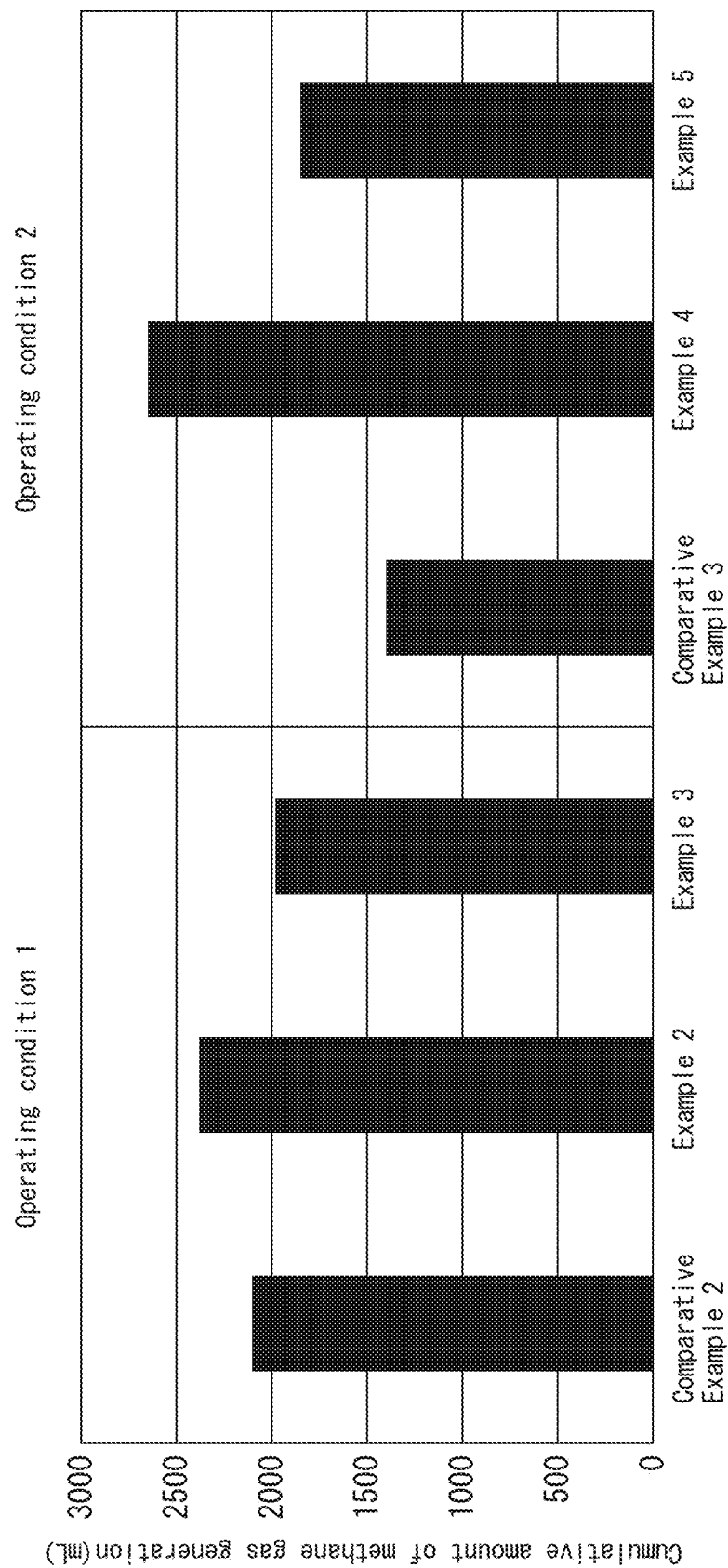

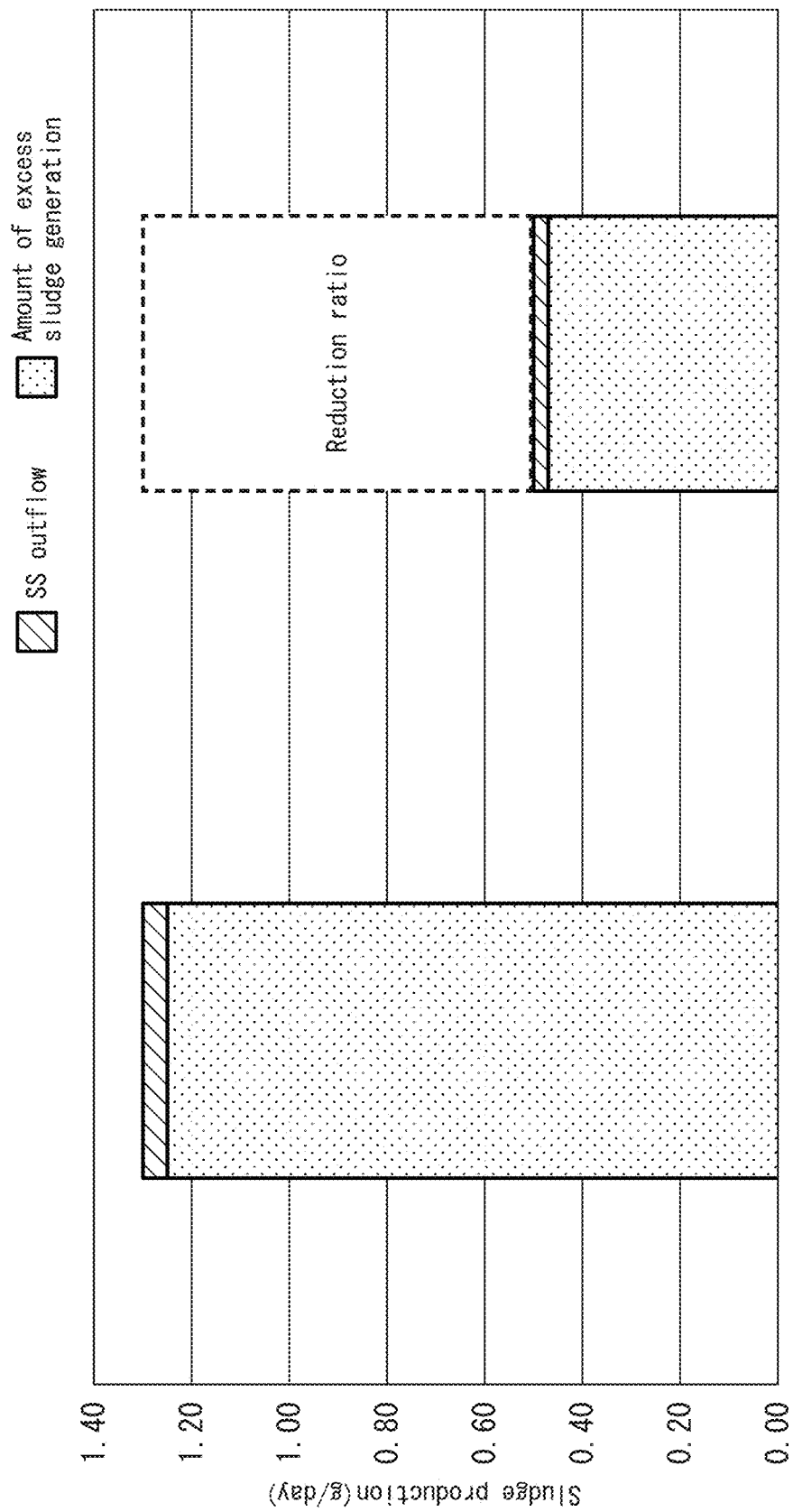

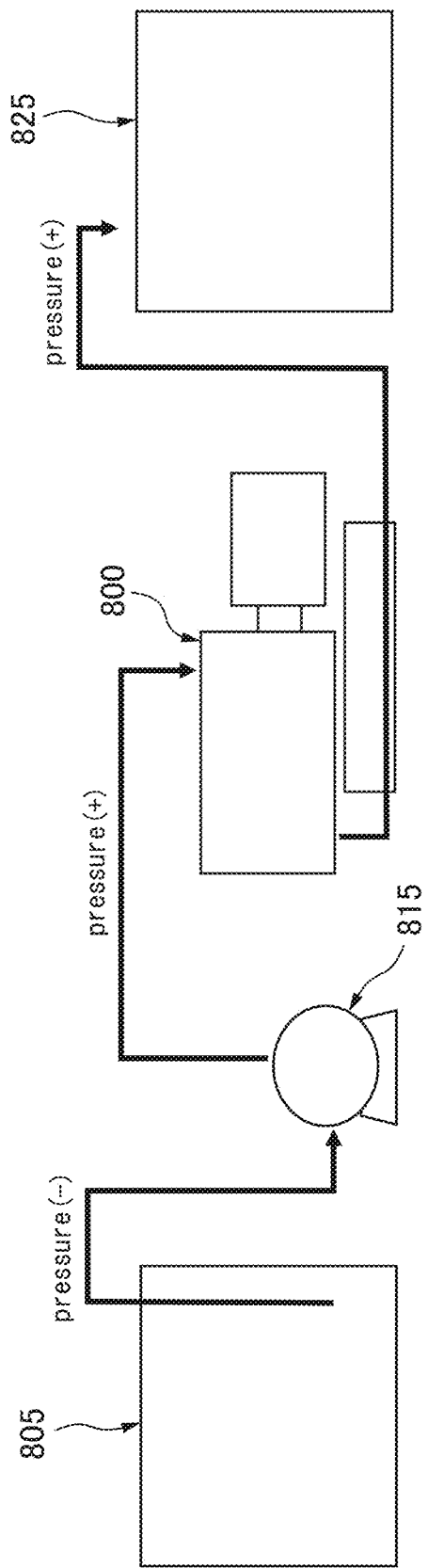

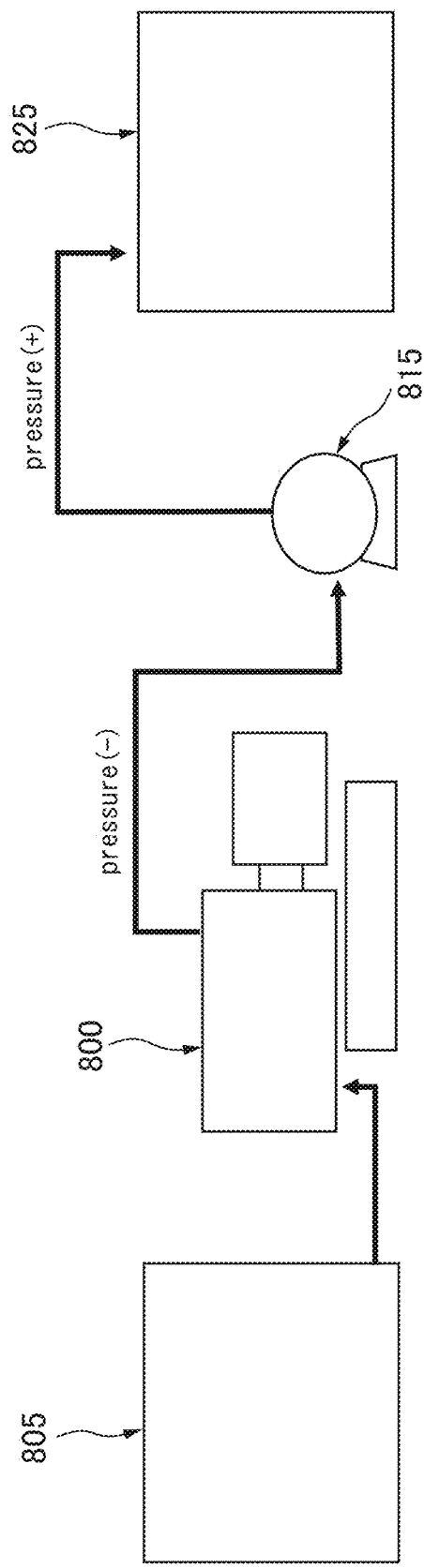

CELL WALL OR CELL MEMBRANE DISRUPTING DEVICE, AND METHOD OF USING THE SAME

The present application is a National Stage Application under 35 U.S.C. § 371 of International Application No. PCT/JP2016/084844 filed on Nov. 24, 2016, which claims the benefit of priority to International Application No. PCT/JP2016/065808, filed on May 27, 2016 in Japan, the disclosures of all of which are hereby incorporated by reference in their entireties.

FIELD

The present disclosure relates to a device for disrupting cell walls and/or cell membranes of microorganisms, algae and the like, and to a method of using the device.

BACKGROUND

Microorganisms, algae and the like present in organic sludge and the like contain a variety of useful resources (for example, proteins, fats and carbohydrates). However, the recovery of such useful resources requires disruption of cell walls and/or cell membranes (hereunder also referred to simply as "cell walls and the like") composing the microorganisms and the like. Because the cell walls and the like composing microorganisms and the like are formed of extremely strong membranes, disruption of the cell walls and the like generally requires advanced techniques and complicated equipment. The conventional methods and equipment have consequently led to increased running cost.

For example, PTL 1 discloses a sludge disrupting device that disrupts sludge generated by biological treatment of organic sewage, the device comprising a rotating disc that rotates at high speed and driving means that drives the rotating disc, and further comprising a fixed disc facing the rotating disc and having a sludge inlet at the center section, wherein a disc gap of at least about 5 mm is provided between the fixed disc and the rotating disc, and the sludge is disrupted primarily by the rotational shearing force of the rotating disc.

PTL 2 discloses a sludge treatment process wherein sludge generated in waste water treatment is subjected to a sludge decomposition step to decompose the sludge, and then to ultrasonic treatment in an ultrasonic treatment step and treatment in a methane fermentation step.

CITATION LIST

Patent Literature

[PTL 1] Japanese Patent Publication No. 3731204
[PTL 2] Japanese Unexamined Patent Publication No. 2002-336898

SUMMARY

Technical Problem

It is desirable to utilize microorganisms, algae and the like for production of biogases (such as methane and hydrogen) and oils; recovery of components such as $CO_2$, phosphorus and nitrogen; and production of foods and cosmetics. For example, there is a demand for achieving volume reduction, conversion to resources and returning to green space, for sludge containing microorganisms, algae and the like. As a result, there is a strong demand for technology for continuously disrupting and degrading microorganisms, algae and the like, and efficiently digesting and/or recovering their components at low cost.

For example, digestion of organic sludge from excess sludge of activated sludge concentration tanks is carried out via solubilization and hydrolysis of microorganisms and the like in the sludge, producing water and carbon dioxide. However, since the rate-determining steps are elution of the intracellular macromolecular substances such as proteins, organic acids, lipids and carbohydrates present in microorganisms, and low molecularization of the substances by hydrolysis, it has required several days of prolonged digestion to digest organic sludge in activated sludge concentration tanks. Consequently, techniques are desired for disrupting cell walls and the like of microorganisms and the like in sludge and achieving low molecularization and solubilization, in order to increase the digestion efficiency of excess sludge and initial sedimentation sludge in activated sludge concentration tanks.

Conventional techniques for disrupting cell walls and the like and achieving low molecularization and solubilization include high energy disruption methods using ultrasonic waves; chemical decomposition methods such as ozone oxidation and alkali treatment; and mechanical disruption methods using a homogenizer or mill. Means for heating to 50° C. or higher are also sometimes employed to facilitate disruption of cell walls and the like.

However, methods utilizing ultrasonic waves, ozone or alkalis are problematic from the standpoint of equipment maintenance control, and increased cost. Mechanical disruption methods with a homogenizer or mill have low treatment efficiency and therefore require large and complicated equipment, thus likewise being problematic in terms of increased cost.

The present disclosure therefore provides a device that can economically and efficiently disrupt cell walls and the like of microorganisms and the like, and a method of using the device.

Solution to Problem

According to one embodiment of the present disclosure, there is provided a cell wall or cell membrane disrupting device comprising a fixed disc, a rotating disc, a rotating shaft for driving of the rotating disc, a pressure reducing means and a housing, wherein at least one pair of the fixed disc and the rotating disc are disposed facing each other, the center section of the fixed disc has a hollow section that is larger than the outer diameter of the rotating shaft passing through the center section, shearing force generated between the rotating disc and the fixed disc is applied to a target fluid having a water content of 89% or higher that has been loaded into the device, and the pressure inside the cell wall or cell membrane disrupting device is reduced to no greater than −0.08 MPa by the pressure reducing means.

According to another embodiment of the present disclosure, there is provided a cell wall or cell membrane disrupting device comprising a fixed disc, a rotating disc, a rotating shaft for driving of the rotating disc, pressure reducing means based on suction force from a land pump and/or a submersible pump, and a housing, wherein at least one pair of the fixed disc and the rotating disc are disposed facing each other, the center section of the fixed disc has a hollow section that is larger than the outer diameter of the rotating shaft passing through the center section, shearing force generated between the rotating disc and the fixed disc is applied to a target fluid having a water content of 89% or higher that has been loaded into the device and, when a land pump is used, the land pump is situated after the discharge port of the device, or when a submersible pump is used, the submersible pump is situated at the discharge port end after the final fixed disc in the device.

According to yet another embodiment of the present disclosure, there is provided a method of reducing sludge volume, comprising a step of treating sludge with the cell wall or cell membrane disrupting device described above.

According to yet another embodiment of the present disclosure, there is provided a method of preparing fertilizer from sludge, the method comprising a step of treating sludge with the cell wall or cell membrane disrupting device described above and a step of converting the treated sludge obtained from the step of treating sludge, to fertilizer.

According to yet another embodiment of the present disclosure, there is provided a method of preparing a culture solution from sludge, the method comprising a step of treating sludge with the cell wall or cell membrane disrupting device described above and a step of collecting the treated separated liquid obtained from the step of treating sludge, as a culture solution.

According to yet another embodiment of the present disclosure, there is provided a deodorizing method comprising a step of treating sewage and/or sludge, or an odorous food, with the cell wall or cell membrane disrupting device described above.

According to yet another embodiment of the present disclosure, there is provided a method of fermenting for obtaining biogas, the method comprising a step of treating sludge with the cell wall or cell membrane disrupting device described above and a step of supplying the treated sludge and/or treated separated liquid obtained from the step of treating sludge, to a biogas fermenter.

According to yet another embodiment of the present disclosure, there is provided a method for producing a food, beverage, drug, supplement or cosmetic, the method comprising a step of treating a target substance containing at least one component selected from the group consisting of fungi, microorganisms, algae and plants (hereunder also referred to "as microorganism groups"), with the cell wall or cell membrane disrupting device described above.

According to yet another embodiment of the present disclosure, there is provided a method for recovering an oil, the method comprising a step of treating a target substance (for example, sludge) containing at least one kind of oil component selected from the group consisting of fungi, microorganisms, algae and plants, with the cell wall or cell membrane disrupting device described above.

Advantageous Effects of Invention

Since the cell wall or cell membrane disrupting device of the present disclosure need only comprise a simple construction including at least a fixed disc, a rotating disc, a rotating shaft for driving of the rotating disc, pressure reducing means and a housing, it is possible to provide a low-cost device with easy equipment maintenance control.

For disruption of cell walls and the like, conventional devices have required an additional equipment for alkali treatment or for heating treatment at 50° C. or higher. However, since the cell wall or cell membrane disrupting device of the present disclosure comprises a pressure reducing means, it does not require provision of equipment for alkali treatment or for heating treatment at 50° C. or higher.

As a result, it is possible to drastically lower running costs compared to conventional devices and equipment.

The cell wall or cell membrane disrupting device of the present disclosure can be used in a method of reducing sludge volume, a method of preparing fertilizer from sludge, a method of preparing a culture solution from sludge, a deodorizing method, a method of fermenting for obtaining biogas, a method for producing a food, beverage, drug, supplement or cosmetic or a method for recovering an oil. The cell wall or cell membrane disrupting device of the present disclosure can sufficiently disrupt cell walls and the like without adversely affecting the active ingredients in the microorganisms and the like, thus allowing the efficiency of each of the aforementioned methods to be improved.

The preceding description should not be construed as disclosing all of the embodiments of the invention nor all of the advantages of the invention.

BRIEF DESCRIPTION OF DRAWINGS

FIG. 5A is a bar graph showing cumulative generation of methane gas in a continuous test under anaerobic conditions.

FIG. 6 is a bar graph showing generation of excess sludge in a continuous test under aerobic conditions.

FIG. 8A is a first schematic diagram of an equipment process comprising a cell wall or cell membrane disrupting device of the present disclosure.

FIG. 8B is a second schematic diagram of an equipment process comprising a cell wall or cell membrane disrupting device of the present disclosure.

DESCRIPTION OF EMBODIMENTS

Figure 1:
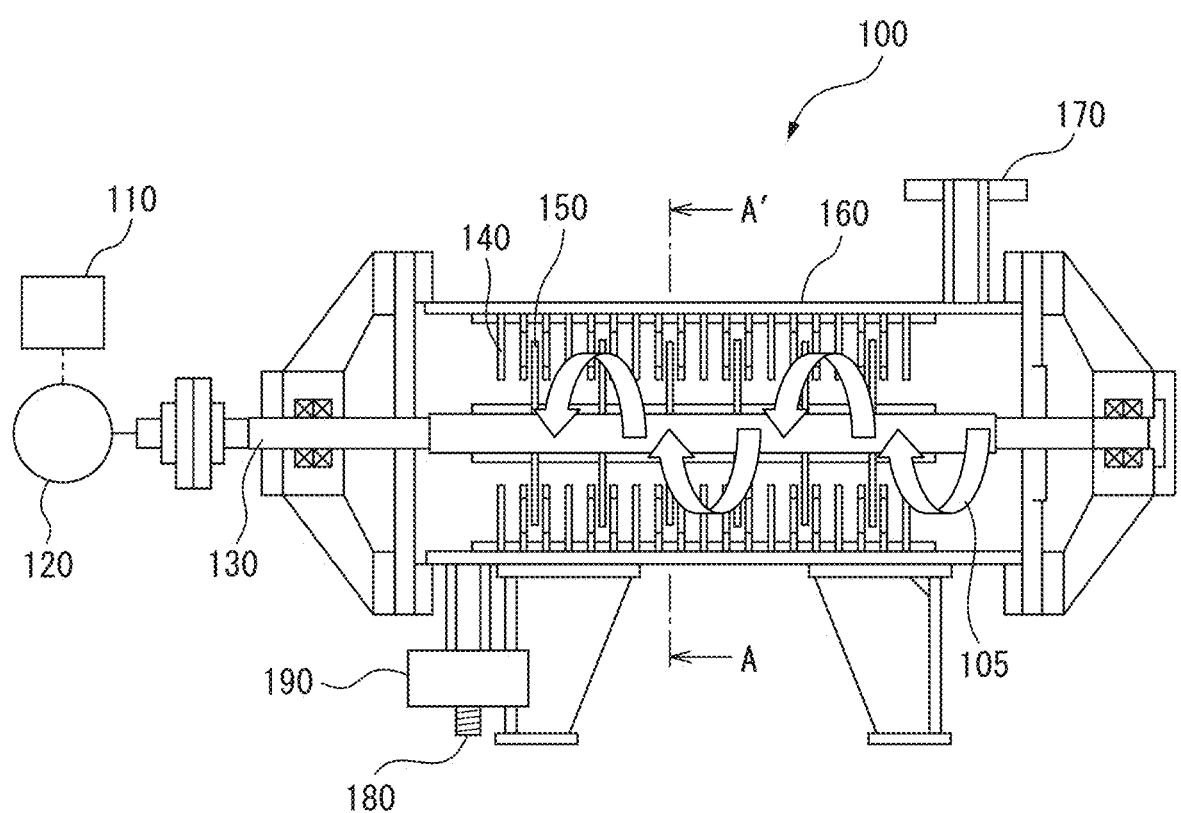
FIG. 1 is a simplified cross-sectional view of a cell wall or cell membrane disrupting device of the present disclosure.

The cell wall or cell membrane disrupting device of the first embodiment of the present disclosure is a cell wall or cell membrane disrupting device comprising a fixed disc, a rotating disc, a rotating shaft for driving of the rotating disc, a pressure reducing means and a housing, wherein at least one pair of the fixed disc and the rotating disc are disposed facing each other, the center section of the fixed disc has a hollow section that is larger than the outer diameter of the rotating shaft passing through the center section, and shearing force generated between the rotating disc and the fixed disc is applied to a target fluid having a water content of 89% or higher that has been loaded into the device. Because the cell wall or cell membrane disrupting device of the present disclosure has a simple construction, the device maintenance control is facilitated and production cost for the device can be reduced. The use of pressure reducing means eliminates the need for equipment for alkali treatment and heating treatment which have been essential in conventional devices, and therefore running cost can be drastically reduced.

The cell wall or cell membrane disrupting device according to the second embodiment of the present disclosure is a cell wall or cell membrane disrupting device comprising a fixed disc, a rotating disc, a rotating shaft for driving of the rotating disc, a pressure reducing means based on suction force from a land pump and/or a submersible pump, and a housing, wherein at least one pair of the fixed disc and the rotating disc are disposed facing each other, the center section of the fixed disc has a hollow section that is larger than the outer diameter of the rotating shaft passing through the center section, shearing force generated between the rotating disc and the fixed disc is applied to a target fluid having a water content of 89% or higher that has been loaded into the device and, when a land pump is used, the land pump is situated after the discharge port of the device, or when a submersible pump is used, the submersible pump is situated at the discharge port end after the final fixed disc in the device. Because the cell wall or cell membrane disrupting device of the present disclosure can reduce the pressure inside the device using a land pump or a submersible pump, without being limited to a vacuum pump, its maintenance is facilitated, and maintenance cost can be drastically reduced compared to using a vacuum pump.

The cell wall or cell membrane disrupting device according to the first or second embodiment can reduce the pressure inside the device to −0.08 MPa or lower by the pressure reducing means. If the pressure inside the device is within this range, a differential pressure will be created between the pressure inside the cell walls and the like and the pressure outside the cell walls and the like, as a condition aiding in disruption of the cell walls and the like. In addition, shearing force between the fixed disc and rotating disc increases as the pressure inside the device drops, facilitating disruption of the cell walls and the like, while cavitation also occurs simultaneously, so that the resulting conditions even further facilitate disruption of the cell walls and the like.

The land pump in the cell wall or cell membrane disrupting device of the second embodiment may be a one rotor screw pump. A one rotor screw pump is preferred for excellent suction force, even among land pumps.

The rotating disc of the cell wall or cell membrane disrupting device according to the first or second embodiment may rotate at a circumferential speed of 10 m/s or greater. If the circumferential speed of the rotating disc is 10 m/s or greater, shearing force between the fixed disc and rotating disc will increase, allowing the cell walls and the like to be more efficiently disrupted.

The cell wall or cell membrane disrupting device according to the first or second embodiment may comprise two or more fixed discs and/or rotating discs. By comprising two or more fixed discs and/or rotating discs, the cell walls and the like can be more efficiently disrupted in a short period of time.

The gaps between the fixed discs and rotating discs of the cell wall or cell membrane disrupting device according to the first or second embodiment may be 5 mm to 30 mm. If the gaps between the fixed discs and rotating discs are within this range, shearing force between the fixed discs and rotating discs will increase, allowing the cell walls and the like to be more efficiently disrupted.

The surfaces of the rotating discs and/or fixed discs in the cell wall or cell membrane disrupting device according to the first or second embodiment may be mirror surfaces or rough surfaces. If the surfaces of the discs are mirror surfaces, the target substance will flow more easily, thus allowing the flow rate of the target substance to be increased, while if they are rough surfaces, the frictional force or surface area of the disc surfaces will be increased, thus allowing the shearing force necessary for disruption of the cell walls and the like to more effectively act on the target substance.

The target substance that is to be loaded into the cell wall or cell membrane disrupting device according to the first or second embodiment may include at least one component selected from the group consisting of fungi, microorganisms, algae and plants. Sludge may also be used as the target substance.

The cell wall or cell membrane disrupting device according to the first or second embodiment can be used in a method of reducing sludge volume, a method of preparing fertilizer from sludge, a method of preparing a culture solution from sludge, a deodorizing method, a method of fermenting for obtaining biogas, a method for producing a food, beverage, drug, supplement or cosmetic or a method for recovering an oil. The cell walls and the like in a target substance including microorganisms and the like that has been treated by the cell wall or cell membrane disrupting device has sufficiently disrupted, and the efficiency of each of the methods described above can therefore be increased.

The following detailed description is for illustration of representative embodiments of the present invention, with reference to the accompanying drawings, with the understanding that the invention is not limited to these embodiments. As regards the reference numerals in the drawings, similarly numbered elements in different drawings indicate similar or corresponding elements.

The term "cavitation", as used throughout the present disclosure, is intended to refer to the phenomenon whereby air bubbles (pockets) are instantaneously generated by gasification of low-pressure regions in a fluid moving through the cell wall or cell membrane disrupting device, and vanish upon collapsing. It is said that the local impact force produced when air bubbles disintegrate during cavitation is 100 MPa to several GPa, and the temperature environment is 1,200° C. or higher. Presumably, a stronger shearing force acts during this time, whereby the cell walls and the like are more easily disrupted.

The term "biogas", as used throughout the present disclosure, refers to a type of biofuel (methane gas, hydrogen gas or the like) that is gas generated by fermentation of sludge and sewage.

The term "sludge", as used throughout the present disclosure, refers to a liquid substance containing final products of organic materials as solids, in which the liquid substance is produced during the treatment process at a sewage treatment plant or during the waste water treatment process at a factory. The term "sludge" also includes "excess sludge" generated by an activated sludge process. When processed liquid that has been treated in an activated sludge reaction tank is introduced into a final sedimentation basin, the "excess sludge" is the portion of activated sludge that has separated by sedimentation, excluding the portion that is returned to the activated sludge reaction tank as return sludge. The excess sludge consists mainly of microorganisms proliferated on dissolved organic matter in the sewage, and protozoans proliferated by preying on the microorganisms.

Throughout the present disclosure, "mixed liquor suspended solids (MLSS)" means the amount of activated sludge in an aeration tank or aerated tank (reaction tank) in an activated sludge process, expressed as mg/L; "mixed liquor volatile suspended solids (MLVSS)" means the volatile solids (VS) among the MLSS, expressed as mg/L; "suspended solids (SS)" means general substances suspended in water; "biochemical oxygen demand (BOD)" means the amount of dissolved oxygen consumed by aerobic microorganisms in water; "total organic carbon (TOC)" means the amount of carbon in organic materials present in water; "dissolved organic carbon (DOC)" means the amount of carbon in organic material dissolved in water; "total nitrogen (T-N)" means the total amount of nitrogen compounds present in water; and "total phosphorus (T-P)" means the total amount of phosphorus compounds present in water. The mixed liquor suspended solids (MLSS) and suspended solids (SS) were measured using a centrifugal separation process, according to a sewerage test method (Japan Sewage Works Association, 1997, 2nd Edition, Chapter 2, Section 12.2).

FIG. 1 shows a simplified cross-sectional view of a cell wall or cell membrane disrupting device 100 according to the first embodiment of the present disclosure. The cell wall or cell membrane disrupting device 100 comprises a housing 160, fixed discs 140 arranged on the inner side of the housing 160, rotating discs 150, a rotating shaft 130 located in the center horizontal direction of the cell wall or cell membrane disrupting device 100, for fixing and driving of the rotating discs 150, a loading port 170, a discharge port 180, and a pressure reducing means 190. The cell wall or cell membrane disrupting device 100 may comprise an inverter 110 and a motor 120 for driving of the rotating shaft 130. The inverter 110 and motor 120 may be integrally formed with the cell wall or cell membrane disrupting device 100, or situated on the outside of the cell wall or cell membrane disrupting device 100. Although an inverter is preferably used to allow appropriate adjustment of the circumferential speed depending on the type and amount of target substance, a star-delta (Y-Δ) type motor and the like may be used instead of an inverter.

Figure 3A:
FIG. 3A is a photomicrograph (150×) of sludge that has been concentrated by centrifugation.
Figure 3B:
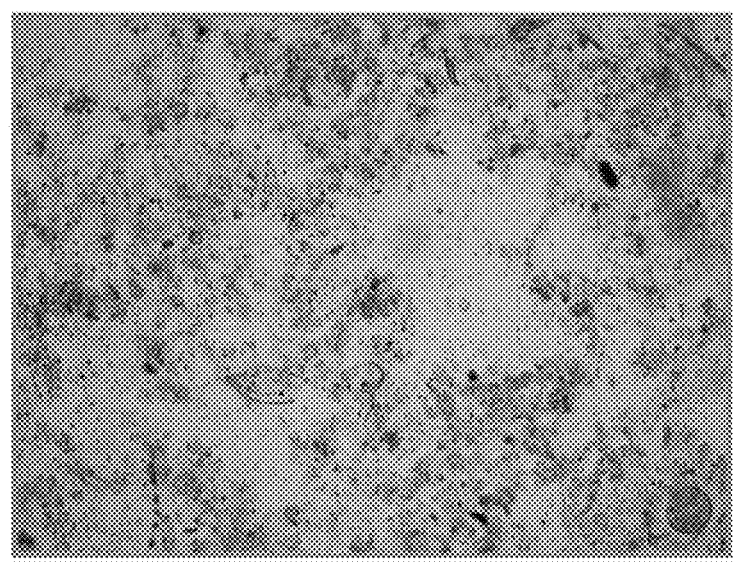
FIG. 3B is a photomicrograph (150×) of sludge after treatment with a cell wall or cell membrane disrupting device.

The target substance loaded into the loading port 170 flows between the fixed discs 140 and rotating discs 150, as indicated by the flow 105 of the target substance in FIG. 1, and is discharged through the discharge port 180. The loading port 170 and discharge port 180 may also be disposed in the opposite manner. Energy such as shearing force produced between the fixed discs 140 and rotating discs 150 and/or between the fixed discs 140 and fixed discs 140 (hereunder also referred to as "between each of the discs"), and between the rotating discs 150 and the inner side of the housing 160 and between the fixed discs 140 and the outer side of the rotating shaft 130, causes disruption of the cell walls and the like of microorganisms and the like in the target substance (FIG. 3A and FIG. 3B).

Figure 2A:
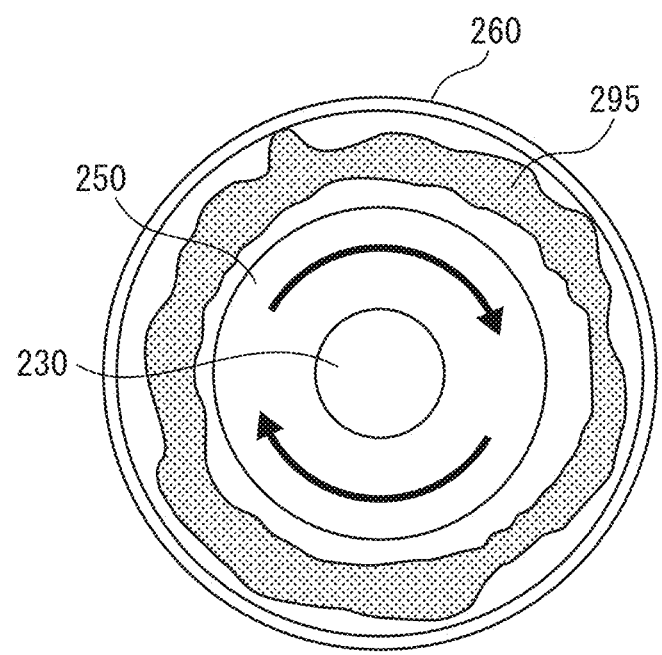
FIG. 2A is an enlarged cross-sectional view of FIG. 1 on plane A-A'.
Figure 2B:
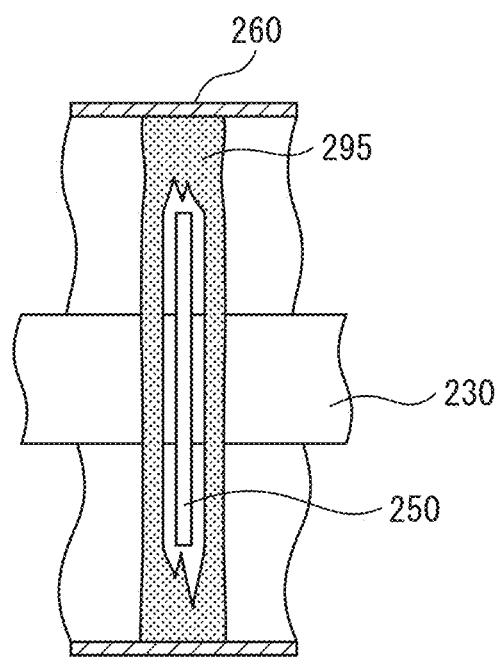
FIG. 2B is an enlarged view of a rotating disc near A-A' of FIG. 1.

Cavitation also occurs between each of the discs in addition to this shearing force, although there is no restriction to this assumption. As an example, FIG. 2A and FIG. 2B show, respectively, an enlarged cross-sectional view on plane A-A' of the cell wall or cell membrane disrupting device 100 of FIG. 1, and an enlarged view of a rotating disc near A-A'. Since the loaded target substance is flowing at high speed inside the device, a low-pressure region is formed in the target substance. The low-pressure region produces air bubbles by gasification of moisture and the like in the target substance, and a cloud 295 (a mixture of liquid and gas) is formed in the target substance. When the air bubbles in the cloud collapse and disappear, an extremely high pressure (impact force) is exerted instantaneously. The energy from the high pressure is also thought to act as shearing force and contribute to disruption of the cell walls and the like.

The components forming the cell wall or cell membrane disrupting device 100 may be made of different materials suited for their purpose. While not being limitative, examples of materials that may be used include one or more selected from the group consisting of metals or metal alloys such as iron and stainless steel, ceramics, glass, plastics, reinforced resins including carbon fibers and/or glass fibers, and rubber. Of these, stainless steel (SUS316, etc.) and ceramics are preferred for their excellent strength and rust-preventing effect.

The surfaces of the components (fixed discs, rotating discs, housing inner wall, rotating shaft outer wall, loading port, discharge port) in contact with the target substance may be treated by water repellent treatment such as fluorine resin coating, hydrophilicizing treatment such as titanium oxide coating or silicon oxide coating, smooth surface (mirror surface) treatment or roughening treatment. Applying water repellent treatment or hydrophilicizing treatment can prevent adhesion of dirt and the like based on the target substance. Applying smooth surface (mirror surface) treatment will aid flow of the target substance, allowing the flow rate of the target substance to be increased. Applying roughening treatment will increase the frictional force and surface area, allowing shearing force and cavitation to be increased. Water-repellent treatment, hydrophilic treatment, smooth surface (mirror surface) treatment and roughening treatment may also be carried out in various combinations. Such treatment may be carried out on all or part of the components used. Roughening treatment may be processing such as embossing, sand blasting, cutting, polishing, laser working or etching, or molding using a concavoconvex die. Alternatively, materials that can be roughened may be attached to the surfaces of the fixed discs, for example, by adhesive, welding, bolting or the like. The rough surfaces may be random irregular shapes, or shapes with grooves having prescribed angles and/or gaps. The sizes and shapes of the rough surfaces may be appropriately adjusted depending on the properties and volume of the target substance to be treated.

The center sections of the fixed discs 140 have large hollow sections with larger outer diameters than the rotating shaft 130 passing through the center section. The fixed discs 140 may have their outer diameters, inner diameters, shapes, thicknesses and number adjusted as appropriate depending on the properties and volume of the target substance loaded into the cell wall or cell membrane disrupting device 100, and the shape and intended design of the housing. In consideration of disruptability of the cell walls and the like, and production cost, the fixed discs 140 preferably have approximately discoid shapes, and the hollow sections of the fixed discs 140 are also preferably essentially circular in shape. The sizes of the hollow sections of the fixed discs 140 may be appropriately adjusted depending on the type and amount of target substance. The surfaces of the fixed discs 140 may have concave or convex inclinations and may also have through-holes on the insides or outer peripheral sections of the discs in addition to the hollow sections at the center sections, in ranges that do not inhibit shearing force and cavitation. The fixed discs 140 may be integrated with the inner wall of the housing 160 by adhesion, welding or the like, or they may be mounted in a removable manner using bolts or the like. The fixed discs 140 and housing 160 may also be formed into an integrated structure from a single material using a 3D printer or the like.

The rotating discs 150 may have their outer diameters, inner diameters, shapes, thicknesses and number adjusted as appropriate depending on the properties and throughput of the target substance loaded into the cell wall or cell membrane disrupting device 100, and the shape and intended design of the housing. In consideration of disruptability of the cell walls and the like and production cost, the rotating discs 150 preferably have approximately discoid shapes. The distance between the outer peripheries of the rotating discs 150 and the inner wall of the housing may also be appropriately adjusted depending on the type and amount of target substance. The surfaces of the rotating discs 150 may have concave or convex inclinations and may also have through-holes on the insides or outer peripheral sections of the discs, in ranges that do not inhibit shearing force and cavitation. The rotating discs 150 may be integrated with the rotating shaft 130 by adhesion, welding or the like, or they may be mounted in a removable manner using bolts or the like. The rotating discs 150 and rotating shaft 130 may also be formed into an integrated structure from a single material using a 3D printer or the like.

The rotational speed and circumferential speed of the rotating discs 150 may be appropriately adjusted depending on the type and amount of the target substance, with no limitation to the following exemplary ranges. The rotational speed of the rotating discs 150 may be 1000 $min^{-1}$ or higher, 2000 $min^{-1}$ or higher or 3000 $min^{-1}$ or higher, and 7000 $min^{-1}$ or lower, 6000 $min^{-1}$ or lower or 5000 $min^{-1}$ or lower. If the rotational speed is within such a range, the circumferential speed of the rotating discs 150 can be adjusted to within the prescribed range. The circumferential speed of the rotating discs 150 may be 20 m/s or higher, 30 m/s or higher or 35 m/s or higher, and 70 m/s or lower, 60 m/s or lower or 55 m/s or lower. If the circumferential speed is within such a range, shearing force for disruption of the cell walls and the like will be efficiently obtained without the inconveniences associated with temperature increase of the target substance. The circumferential speed is preferably in the range of 37 to 52 m/s as production of shearing force and also cavitation will be facilitated.

The fixed discs 140 in the cell wall or cell membrane disrupting device 100 of the present disclosure have hollow sections at the center sections (target substance suctioning holes), and are disposed facing the rotating discs 150. The fixed discs 140 have the function of creating a flow in which the target substance that has flowed in the outer peripheral directions of the rotating discs 150 passes again through the hollow sections of the fixed discs 140 by centrifugal force of the rotating discs 150, and also flows into the center sections of the rotating discs 150. In other words, the fixed discs 140 function to homogenize the target substance in the cell wall or cell membrane disrupting device 100.

The cell wall or cell membrane disrupting device 100 of the present disclosure may comprise one or more each of the fixed discs 140 and rotating discs 150, but from the viewpoint of efficiency for disruption of the cell walls and the like, it preferably comprises two or more of these discs. In this case, the fixed discs and rotating discs may be alternately arranged, or may be arranged with two or more fixed discs between each pair of rotating discs. The sizes and shapes of the arranged rotating discs and fixed discs may be mutually identical or different.

The gaps between the fixed discs and rotating discs or the gaps between fixed discs should be determined based on the sizes (inner diameters and outer diameters) of the rotating discs and fixed discs used, the rotational speed of the rotating discs, or the properties and volume of the target substance, but they are preferably 5 mm or larger, 7 mm or larger or 9 mm or larger, and 30 mm or smaller, 20 mm or smaller or 15 mm or smaller, although this is not particularly limitative for the invention. In consideration of shearing force and cavitation, the range of 10 mm to 11 mm is preferred. The gaps between each of the discs may be consistent or varying, but are preferably varying. The gaps between each of the discs may be continuously, stepwise or partially increasing from the loading port end toward the discharge port end. For example, it may increase in a stepwise manner, with the gaps between the discs being 10 mm from the loading port up to near the center section of the device, and the gaps between the discs being 11 mm from near the center section of the device up to the discharge port. If the gaps between the discs near the loading port are narrow, the flow rate of the target substance will increase and disruptability of cell walls and the like will be improved. On the other hand, if the gaps between the discs are large near the discharge port, the flow rate of the target substance will be more gentle, helping to prevent clogging of the target substance in the device.

The cell wall or cell membrane disrupting device 100 of the present disclosure may further comprise disc gap adjusting means whereby the disc gaps are adjusted. Employing disc gap adjusting means allows the disc gaps to be optimally adjusted in consideration of the properties of the target substance to be treated, thus allowing even more effective use of the cell wall or cell membrane disrupting device of the present disclosure.

The rotating shaft 130 is situated in the center horizontal direction of the cell wall or cell membrane disrupting device 100, and it serves to fix and drive the rotating discs 150. The rotating shaft 130 may also be provided with the pressure reducing means 190 described below. If the pressure can be reduced through the rotating shaft 130, then the pressure can be reduced in a uniform manner inside the device.

The housing 160 is a component covering the outer periphery of the cell wall or cell membrane disrupting device 100, and its shape, size and constituent materials may be selected as appropriate for the purpose of use of the device. In consideration of producing shearing force, and also production cost, a cylindrical housing made of stainless steel (SUS316, etc.) is preferred.

The pressure reducing means 190 has the function of creating differential pressure inside and outside of the cells of the microorganisms and the like, thus facilitating disruption of cell walls and the like. Employing pressure reducing means 190 also eliminates the need to use alkali treatment or heating treatment at 50° C. or higher, which is used in the prior art for disruption of cell walls and the like. It is therefore possible to minimize equipment space while also greatly reducing running cost, compared to conventional devices and equipment. However, alkali treatment or heating treatment at 50° C. or higher may be used for the cell wall or cell membrane disrupting device 100 of the present disclosure. Needless to mention, using such treatment in combination will further increase disruption of cell walls and the like compared to conventional devices and equipment.

The reduced pressure conditions inside the cell wall or cell membrane disrupting device may be appropriately adjusted depending on the type and amount of target substance, and they may be as follows, though this is not limitative. The pressure inside the cell wall or cell membrane disrupting device may be reduced to −0.1 MPa or lower, −0.09 MPa or lower or −0.08 MPa or lower by pressure reducing means. Particularly in consideration of producing shearing force and cavitation, the pressure is preferably −0.080 MPa (−80 kPa) or lower, −0.065 MPa (−65 kPa) or lower or −0.060 MPa (−60 kPa) or lower. While there is no particular limitation for the lower limit of the pressure, it may be −0.01 kPa (−0.00001 MPa) or higher, −0.05 kPa (−0.00005 MPa) or higher or −0.1 kPa (−0.0001 MPa) or higher. The pressure range is preferably −0.01 kPa to −0.080 MPa, more preferably −0.05 kPa to −0.065 MPa and even more preferably −0.1 kPa to −0.060 MPa. These pressure values are expressed as gauge pressure, based on atmospheric pressure as zero. Here, "pressure reduction" is intended as a concept including negative pressure.

The pressure reducing means 190 is not particularly restricted, and a vacuum pump such as a rotary pump or dry pump, for example, may be used. The pressure reducing means 190 may be provided integrally with the cell wall or cell membrane disrupting device 100. In such a case, the pressure reducing means 190 may be disposed at one or more locations selected from the group consisting of the loading port 170, housing 160, rotating shaft 130 and discharge port 180. Alternatively, the pressure reducing means 190 may be disposed separately from the cell wall or cell membrane disrupting device 100. In such a case, the pressure reducing means 190 may be disposed, via piping or the like, at one or more locations selected from the group consisting of the loading port 170, housing 160, driving means 130 and discharge port 180.

By employing a land pump and/or a submersible pump it is possible to reduce the pressure inside the cell wall or cell membrane disrupting device. A construction using a land pump as an example will now be explained with reference to FIG. 8A and FIG. 8B, with no limitation to this construction. In FIG. 8A, a land pump 815 is installed between a pre-treatment storage tank 805 in which the target substance such as sludge is stored, and the cell wall or cell membrane disrupting device 800. The land pump used may be a one rotor screw pump, for example. A one rotor screw pump is preferred for excellent suction performance. The one rotor screw pump used may be a Mohno Pump® by Heishin, Ltd. With this configuration, the target substance such as sludge that has been conveyed by the land pump 815 is loaded into the cell wall or cell membrane disrupting device 800 in a pressurized state. For this configuration, therefore, a vacuum pump as described above is preferably used as appropriate for the cell wall or cell membrane disrupting device. In FIG. 8B, on the other hand, a land pump 815 is installed between the cell wall or cell membrane disrupting device 800 and a post-treatment storage tank 825 that stores the target substance that has been treated by the device. With this configuration, the cell wall or cell membrane disrupting device 800 is subjected to suction force from the land pump 815, and therefore the inside of the device is reduced in pressure. In order to adequately exhibit the suction force from the land pump 815, the cell wall or cell membrane disrupting device 800 is preferably completely filled with the target substance. In the case of a common land pump, the suction force is weak, which may impose restrictions on its installation, and therefore a one rotor screw pump type having excellent suction force is preferred. For this configuration, therefore, the preferred construction is such that the target substance is loaded from below the device and discharged from above (the flow 105 of the target substance in FIG. 1 is in the reverse direction, with 170 representing the discharge port and 180 representing the loading port). With the configuration shown in FIG. 8B, the pressure can be reduced with the land pump alone without using a vacuum pump, and therefore the equipment can be simplified in comparison to the configuration of FIG. 8A. However, the vacuum pump may also be used in combination in the construction of FIG. 8B. The construction of FIG. 8B is designed so that target substance is loaded from the bottom of the pre-treatment storage tank into the cell wall or cell membrane disrupting device 800 using the weight of the target substance itself, and therefore the land pump 815 is not installed between the pre-treatment storage tank 805 and the cell wall or cell membrane disrupting device 800. However, the land pump 815 may also be installed between the pre-treatment storage tank 805 and the cell wall or cell membrane disrupting device 800 as in FIG. 8A, for a construction in which the target substance is removed from the top of the pre-treatment storage tank. Incidentally, while FIG. 8B shows an example wherein the land pump 815 is installed between the cell wall or cell membrane disrupting device 800 and the post-treatment storage tank 825, the land pump 815 only needs to be installed downstream from the discharge port of the cell wall or cell membrane disrupting device 800. Not only the post-treatment storage tank 825, but also various processing devices may be situated downstream from the land pump 815, or the downstream end of the land pump 815 may be directly connected to different prescribed facilities. When a submersible pump is used, the submersible pump may be installed at a location that is submerged in the target substance at the discharge port end, after the final fixed disc in the cell wall or cell membrane disrupting device 800.

The cell wall or cell membrane disrupting device 100 of the present disclosure may further comprise a heating means. The heating means used may be heating means at 50° C. or higher, as used in the prior art. However, the heating means at 170° C. or higher, 150° C. or higher or 120° C. or higher is preferably not employed because of increased energy cost, and the potential for problems occurring in the cell wall or cell membrane disrupting device. The heating means at 30° C. or higher and lower than 50° C. can also be used, which has not been used in the prior art. Conventional heating means at 50° C. or higher is used for the purpose of softening cell walls and the like. The heating means at 30° C. or higher and lower than 50° C., on the other hand, is used for the purpose of efficiently creating cavitation. Since the cell wall or cell membrane disrupting device 100 of the present disclosure comprises pressure reducing means 190, cavitation is easily produced even with heating at 30° C. or higher and lower than 50° C., thus further improving disruption of cell walls and the like.

The heating means used may be publicly known means such as a steam jacket, a heater, exhaust heat emitted from equipment, solar heat, geothermal heat or soil heat. The heating means may be provided integrally with the cell wall or cell membrane disrupting device, or it may be situated separately from the device.

The target substance to be loaded into the cell wall or cell membrane disrupting device of the present disclosure is a liquid fluid having a water content of 89% or higher, 90% or higher or 91% or higher. If the water content of the target substance is less than 89%, it will be a highly viscous clay-like (sludge-like) substance, and especially if it is 80% or lower, it will itself be carriable as a substance and will no longer be disruptable using the cell wall or cell membrane disrupting device of the present disclosure. The target substance also contains at least one component selected from the group (group of microorganisms) consisting of fungi, microorganisms, algae, and plants such as vegetable scrap and non-standard vegetables. Specifically, the target substance used may be, for example, sludge (organic sludge), sewage, culture solutions obtained by artificially culturing at least one component of the group of microorganisms, cultured products obtained by dehydrating treatment of such culture solutions, concentrates or concentrated substances obtained by concentrating at least one component of the group of microorganisms, and odorous foods such as konjak obtained by processing konjak potato. The target substance may be loaded directly into the cell wall or cell membrane disrupting device, or it may be loaded after addition of water or dehydration for adjustment to a suitable solid content (water content).

The cell wall or cell membrane disrupting device of the present disclosure may be used for various purposes such as the following, which are not limitative.

The cell wall or cell membrane disrupting device of the present disclosure may be used for volume reduction of sludge. The sludge that has been treated by the cell wall or cell membrane disrupting device has the cell walls and the like of microorganisms and the like in the sludge disrupted. As a result, components in the cells such as proteins, carbohydrates, fats, nitrogen, phosphorus and $H_2O$ elute out and undergo low molecularization. Since the water eluted by hydrolysis can be removed by a subsequent dewatering step, low molecularization to $H_2O$ can contribute to reducing the sludge water content. Moreover, since components such as proteins undergo low molecularization and solubilize in the sludge, it is possible to improve digestion efficiency with a digester containing methanogenic bacteria used for sewage treatment, from the conventional level of about 40% to 60-80%. Thus, the amount of sludge produced from the digester can be drastically reduced.

Microorganisms and the like in sludge treated by the cell wall or cell membrane disrupting device of the present disclosure are efficiently disrupted and lowered in molecular weight to components such as nitrogen, phosphorus and $H_2O$, as explained above. The dehydrated sludge contains more abundant fertilizer components such as nitrogen and phosphorus than conventional sludge, and therefore fertilizer of excellent quality can be obtained.

Microorganisms and the like in sludge treated by the cell wall or cell membrane disrupting device of the present disclosure are efficiently disrupted and lowered in molecular weight to components such as nitrogen, phosphorus and $H_2O$, as explained above. These components are also abundantly present in the treated separated liquid obtained from treated sludge. Since low molecularized components are efficiently absorbed by algae and microorganisms and the like, they can be effectively utilized as culture solution for algae and microorganisms and the like. In particular, because algae carry out photosynthesis, improving the culturing efficiency of algae contributes to carbon offset of the greenhouse gas $CO_2$.

With sewage and/or sludge that has been treated with the cell wall or cell membrane disrupting device of the present disclosure, the microorganisms and the like in the sludge or sewage are efficiently disrupted and lowered in molecular weight to components such as nitrogen, phosphorus and $H_2O$, as explained above, and therefore odor can be eliminated. The deodorizing performance can be appropriately adjusted by specifying the rotational speed of the rotating discs, in consideration of the type, loading amount and temperature of the target substance. The deodorizing treatment can also be applied when the target substance is an odorous food such as konjak.

Microorganisms and the like in sludge treated by the cell wall or cell membrane disrupting device of the present disclosure are efficiently disrupted and lowered in molecular weight to components such as proteins, carbohydrates and fats, as explained above. Since the components obtained by low molecularization can drastically improve the metabolic efficiency of methanogens, hydrogen-producing bacteria and the like, it is possible to improve the fermentation efficiency for biogases such as methane and hydrogen, to over twice the conventional level. For example, the amount of methane gas generated using treated sludge and/or treated separated liquid that has been treated by the cell wall or cell membrane disrupting device can be increased by 2 to 3 times compared to non-treated sludge. $CO_2$ can be increased proportionally, and the fermentation period can also be shortened compared to the prior art. The generated $CO_2$ can be recovered and used for culturing of algae and the like.

In addition to the microorganisms and the like in sludge, other fungi, microorganisms, algae and plants and the like treated by the cell wall or cell membrane disrupting device of the present disclosure are also disrupted and lowered in molecular weight to components such as carbohydrates, fats, nitrogen, phosphorus and $H_2O$. The components that have been lowered in molecular weight are absorbed with high efficiency through the digestive system and skin of humans and animals. Therefore, fungi, microorganisms, algae and plants and the like that have been treated by the cell wall or cell membrane disrupting device are beneficial for use in foods, beverages, drugs, cosmetics and supplements and the like.

The cell wall or cell membrane disrupting device of the present disclosure can treat target substances such as fungi, microorganisms, algae and plants such as rapeseed, that contain oils to be used as various fuels, for example. Treatment of an oil-containing target substance by the cell wall or cell membrane disrupting device of the present disclosure allows the oil to be recovered very efficiently.

Using pressure reducing means in the cell wall or cell membrane disrupting device of the present disclosure eliminates the need for a conventional pH adjusting tank or means for heating to 50° C. or higher. The low molecularized components thus do not undergo degeneration or decomposition, allowing the components to be more efficiently utilized than with conventional devices.

EXAMPLES

Instances of specific embodiments of the present disclosure will now be described as Examples, with the understanding that they are not limitative on the invention.

<Biodegradable Test Under Anaerobic Conditions>

Example 1

Excess sludge was treated using a cell wall or cell membrane disrupting device having the construction shown in FIG. 1 (with 170 as the discharge port, 180 as the loading port, and employing a one rotor screw pump and vacuum pump downstream from the discharge port, instead of pressure reducing means 190). The treatment conditions were a rotating disc rotational speed of 3500 min$^{-1}$, a circumferential speed of 50 m/s, reduced pressure conditions of –0.01 MPa and a treatment time of 60 minutes. In order to reproduce the anaerobic treatment that is commonly employed in the field of sewage treatment, a batch experiment was carried out using a vial. The anaerobic treatment was a biological process of decomposing organic materials in sludge and converting them to methane gas, by the metabolic action of microorganisms such as methanogens under oxygen-free anaerobic conditions.

In a vial (75 mL) having the interior exchanged with nitrogen gas, there were loaded 20 mL of seed sludge (digested sludge) containing methanogens, and as substrate, 20 mL of excess sludge obtained from treatment with a cell wall or cell membrane disrupting device, and the amount of methane gas generated was periodically measured after setting in a constant temperature shaking tank (water temperature: 36° C., shaking frequency: 100 times/min). The results are shown in FIG. 4A and FIG. 4B.

Comparative Example 1

In a vial (75 mL) having the interior exchanged with nitrogen gas, there were loaded 20 mL of digested sludge, and as substrate, 20 mL of excess sludge which is not treated with a cell wall or cell membrane disrupting device, and the amount of methane gas generated was periodically measured after setting in a constant temperature shaking tank (water temperature: 36° C., shaking frequency: 100 times/min). The results are shown in FIG. 4A and FIG. 4B.

Figure 4A:
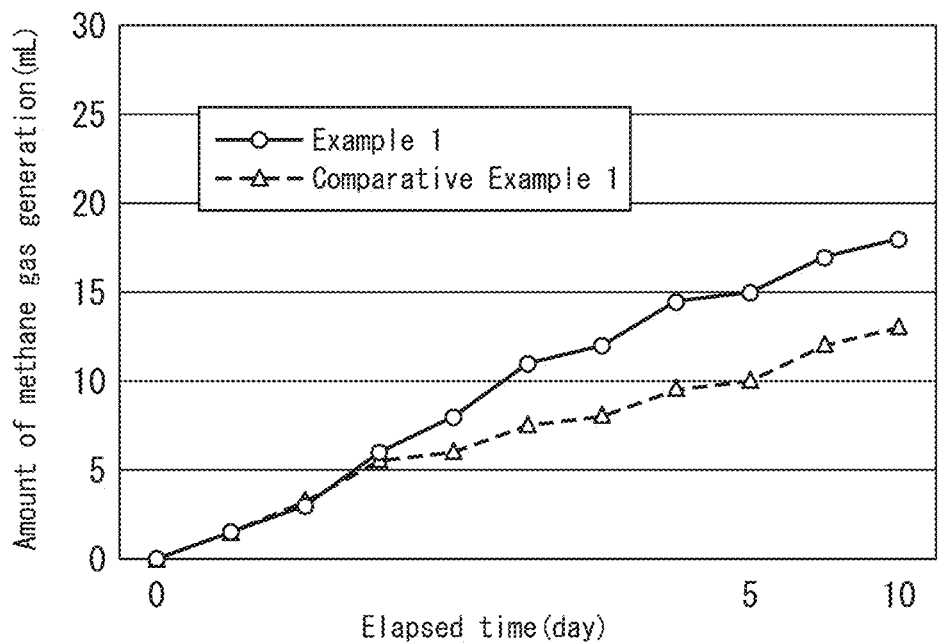
FIG. 4A is a graph showing cumulative generation of methane gas in a batch test under anaerobic conditions.
Figure 4B:
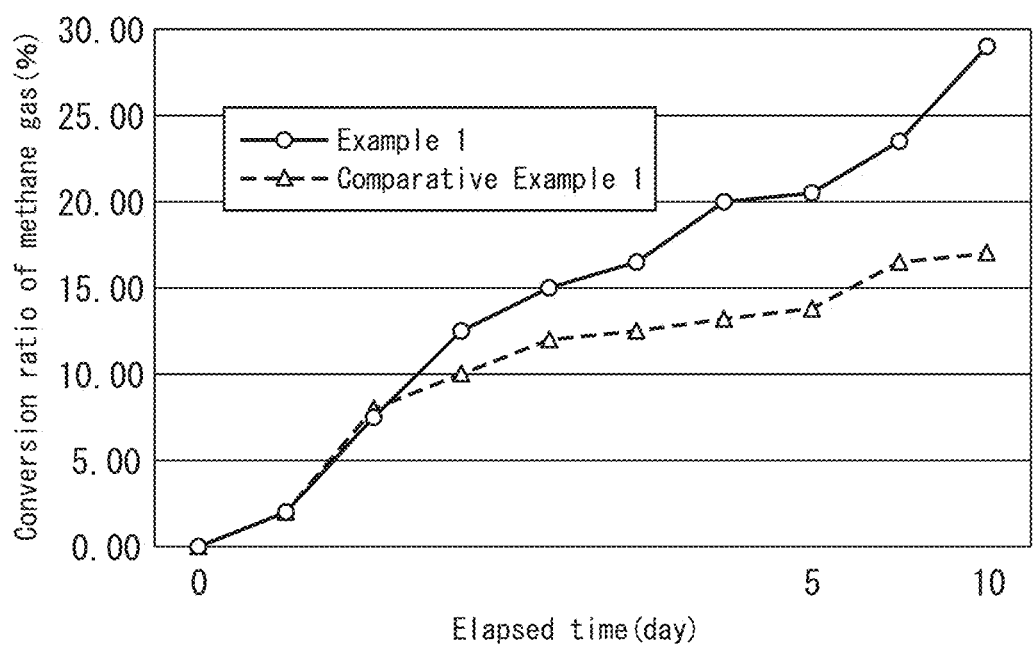
FIG. 4B is a graph showing conversion efficiency to methane gas in a batch test under anaerobic conditions.

FIG. 4A shows cumulative generation of methane gas as a function of elapsed time, and FIG. 4B shows the methane gas conversion ratio as a function of elapsed time. The methane gas conversion ratio represents the degree to which the loaded substrate could be converted to methane gas. For FIG. 4B, the amount of gas generated by autodigestion of the loaded digested sludge was subtracted. As seen in FIG. 4A and FIG. 4B, it was confirmed that in the system where excess sludge was loaded after treatment with the cell wall or cell membrane disrupting device, methane gas generation and conversion were drastically increased.

<Continuous Biodegradable Test Under Anaerobic Conditions>

Example 2 to Example 5, Comparative Example 2 and Comparative Example 3

Figure 5B:
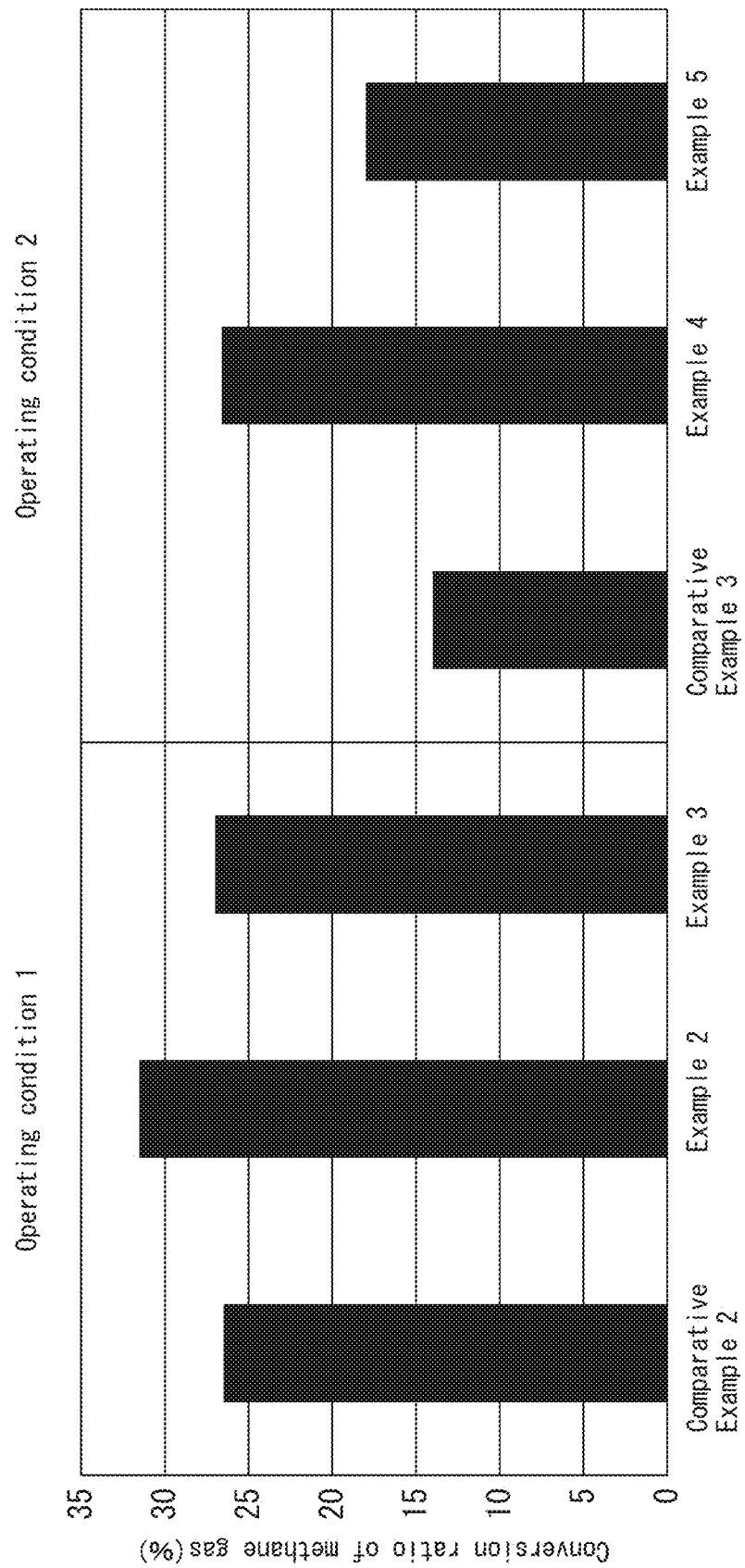
FIG. 5B is a bar graph showing conversion efficiency to methane gas in a continuous test under anaerobic conditions.

Actual anaerobic treatment is carried out in a continuous manner. Therefore, for a model experiment of continuous anaerobic treatment, an experiment apparatus was used having a construction with two parts: a digestion bottle in which digested sludge and substrate (excess sludge before treatment or excess sludge after treatment with the cell wall or cell membrane disrupting device) were mixed and subjected to anaerobic treatment, and a generated gas measuring device for collection of the generated gas on water. As seed sludge, 1.5 L of digested sludge was loaded into the digestion bottle (2 L) which had the interior exchanged with nitrogen gas. The operating conditions for the continuous biodegradable test are shown in Table 1. The digested sludge and substrates used under each of the operating conditions are shown in Table 2. The digested sludge was sampled from the digestion bottle once a day, in the amounts listed in Table 1. After sampling, an amount of substrate equal to the sampled amount was added to the digestion bottle. The excess sludge treated with the cell wall or cell membrane disrupting device that was used as substrate was the treated sludge obtained in Example 1. During the experiment, the digestion bottle was maintained at approximately 36° C. while stirring with a stirrer. The mixed liquor suspended solids (MLSS) and mixed liquor volatile suspended solids (MLVSS) of each sample were measured. The results are shown in Table 3. The percentages reduction of MLSS and MLVSS are shown in Table 3, expressed as relative values with respect to the untreated sludge (Comparative Examples 2 and 3). FIG. 5A shows comparative data for cumulative generation of methane gas, and FIG. 5B shows comparative data for the conversion ratio of methane gas.

TABLE 1

| Operating conditions | | Substrate | Residence time | Sampling volume | Temperature |
|---|---|---|---|---|---|
| 1 | Comp. Ex. 2 | Untreated sludge | 20 days | 75 mL | 36° C. |
|   | Example 2 | Treated sludge | 20 days | 75 mL | 36° C. |
|   | Example 3 | Treated sludge | 10 days | 150 mL | 36° C. |
| 2 | Comp. Ex. 3 | Untreated sludge | 10 days | 150 mL | 36° C. |
|   | Example 4 | Treated sludge | 10 days | 150 mL | 36° C. |
|   | Example 5 | Treated sludge | 5 days | 300 mL | 36° C. |

TABLE 2

| Operating conditions | Sludge | MLSS (mg/L) | MLVSS (mg/L) | Treated solubilization rate (%) |
|---|---|---|---|---|
| 1 | Digested sludge | 15,100 | 9800 | — |
|   | Excess sludge | 13,900 | 10,000 | 37.0 |
| 2 | Digested sludge | 18,000 | 11,300 | — |
|   | Excess sludge | 22,500 | 14,600 | 36.0 |

From FIG. 5A and FIG. 5B, it is seen that, under the same residence time (Example 2 and Comparative Example 2, Example 4 and Comparative Example 3), the cumulative generation of methane gas and conversion ratio of methane gas were both increased, and therefore the biodegradability of the sludge had been increased by the cell wall or cell membrane disrupting device. Also, FIG. 5B shows that the treated sludge (Example 3) had similar values as the untreated sludge (Comparative Example 2), under operating conditions 1. The treated sludge (Example 4) also exhibited the highest values under operating conditions 2 as well. From these results, it was confirmed that the conversion time to methane gas can be shortened by 10 days or more compared to the prior art embodiment which did not employ a cell wall or cell membrane disrupting device.

TABLE 3

| Operating conditions | | Substrate | Residence time | MLSS reduction rate | MLVSS reduction rate |
| --- | --- | --- | --- | --- | --- |
| 1 | Comp. Ex. 2 | Untreated sludge | 20 days | 1.00 | 1.00 |
| | Example 2 | Treated sludge | 20 days | 1.33 | 1.26 |
| | Example 3 | Treated sludge | 10 days | 1.20 | 1.17 |
| 2 | Comp. Ex. 3 | Untreated sludge | 10 days | 1.00 | 1.00 |
| | Example 4 | Treated sludge | 10 days | 1.10 | 1.17 |
| | Example 5 | Treated sludge | 5 days | 0.71 | 0.87 |

As seen from Table 3, under operating conditions 1, the reduction rate in MLSS and MLVSS of the treated sludge (Example 3) increased 1.20-fold and 1.17-fold, respectively. Under operating conditions 2 as well, the reduction rate in MLSS and MLVSS of the treated sludge (Example 4) increased 1.10-fold and 1.17-fold, respectively. Incidentally, Example 5 had inferior results for reduction rate in both MLSS and MLVSS compared to Comparative Example 3. Presumably, this is because in Example 5, the substrate load with respect to seed sludge was too high, preventing thorough digestion. As demonstrated by these results, the final treatment period for sludge can be shortened by 10 days or more compared to the prior art embodiment which did not employ a cell wall or cell membrane disrupting device.

<Biodegradable Test Under Aerobic Conditions>

Example 6

The experiment device for aerobic treatment had a construction with two parts: an aeration tank and a settling tank. The loaded substrate glucose, as the main carbon source, was supplied into the aeration tank at an inflow BOD of approximately 200 mg/L. The operating conditions were set to: 20 L of activated sludge loaded into the aeration tank, a residence time of 24 hours and an MLSS in the aeration tank of 1,000 to 2,000 mg/L. The continuous experiment was carried out for 20 days. After concentrating the excess sludge produced during the process, the substance treated with the cell wall or cell membrane disrupting device was returned into the aeration tank, and the amount of excess sludge generated and the water quality inside the aeration tank, and that of the treated water, were examined. The treatment conditions with the cell wall or cell membrane disrupting device were the same as in Example 1. The results are shown in FIG. 6, Table 4 and Table 5. The sludge was sampled once per day from the treated water and aeration tank, and the MLSS, SS (suspended solids), total organic carbon (TOC), biochemical oxygen demand (BOD), dissolved organic carbon (DOC), total nitrogen (T-N) and total phosphorus (T-P) were measured.

Comparative Example 4

As a control, ordinary aerobic treatment was carried out without removing out the sludge. The results are shown in FIG. 6, Table 4 and Table 5.

TABLE 4

Comparison of change in MLSS

| | Initial (mg/L) | Final (mg/L) |
| --- | --- | --- |
| Comp. Example 4 | 950 | 1700 |
| Example 6 | 910 | 1370 |

TABLE 5

Comparison of water quality of treated water

| | Comp. Example 4 (mg/L) | Example 6 (mg/L) |
| --- | --- | --- |
| SS | 4.1 | 2.1 |
| BOD | 8.6 | 5.4 |
| TOC | 6.6 | 2.1 |
| DOC | 5.4 | 1.3 |
| T-N | 4.1 | 3.6 |
| T-P | 22.4 | 19.5 |

As seen in FIG. 6, the system of Example 6 had 62% reduction in sludge production compared to the system of Comparative Example 4. Presumably, this is because the sludge that had been treated with the cell wall or cell membrane disrupting device and returned to the aeration tank had been efficiently biodegraded and reduced in volume. As seen in Table 4, the system of Example 6 was confirmed to have lower MLSS from start to finish, compared to the system of Comparative Example 4. As also seen in Table 4, the water quality of the treated water of Example 6 was virtually identical to that of Comparative Example 4, thus confirming that the system of Example 6 had been operating in a satisfactory state. These results indicate that a cell wall or cell membrane disrupting device does not affect deterioration of the water quality of treated water. Incidentally, a high T-P value was exhibited in both Comparative Example 4 and Example 6. Presumably, this occurred because the T-P was high at 26 mg/L in the inorganic salts loaded together with the glucose substrate, such that the T-P in the inorganic salts in the tank flowed out as treated water without being treated. It was thus confirmed that a cell wall or cell membrane disrupting device can aid in biodegradation of sludge under aerobic conditions.

<Test of Lipid Extraction and Hydrogen Production from Algae>

Example 7

Figure 7A:
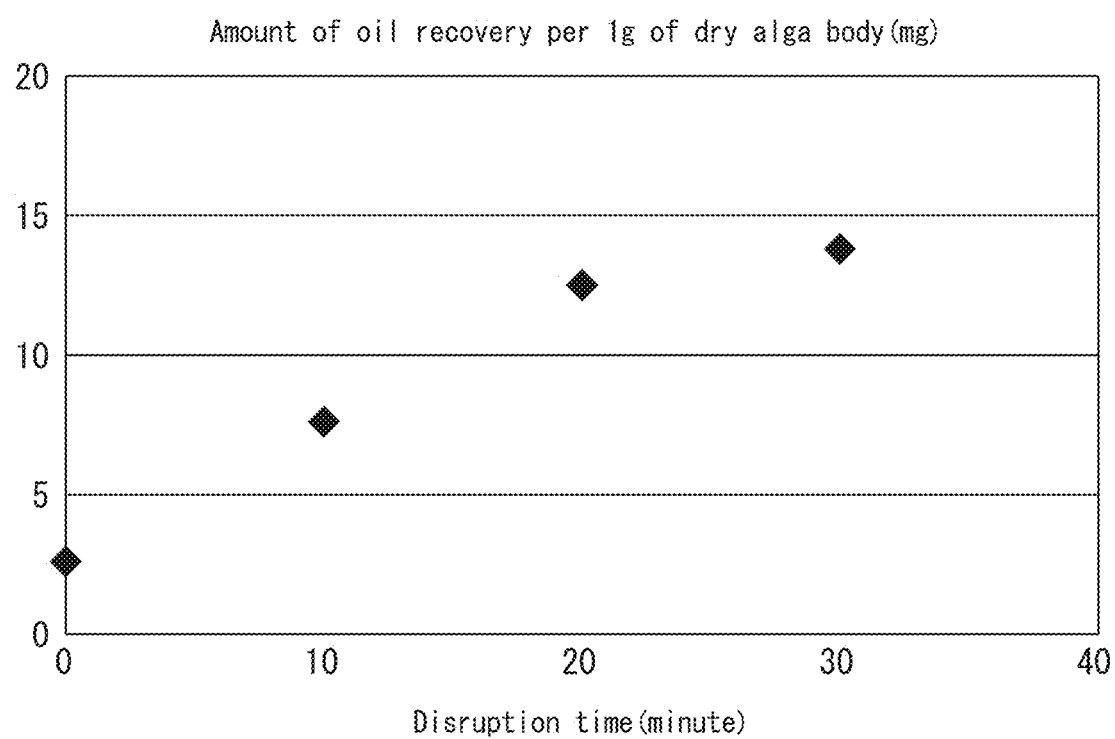
FIG. 7A is a graph showing the correlation between disruption treatment time (min) and oil recovery (mg) per 1 g of dry alga body.

A high-density cultured algae culture solution was treated with a cell wall or cell membrane disrupting device. The treatment conditions with the cell wall or cell membrane disrupting device were the same conditions as Example 1, except that the treatment time was changed to 10 minutes, 20 minutes and 30 minutes. After collecting 100 mL of disrupted algae culture solution and undisrupted algae culture solution into separate beakers, the nanobubbles were aerated through each beaker for 10 seconds to recover the lipids from the algae. The results are shown in FIG. 7A. As seen in FIG. 7A, it was confirmed that it is possible to efficiently recover lipids from an algae culture solution when the treatment time is about 20 to 30 minutes. Incidentally, recovery treatment using nanobubbles is not limited to algae lipid recovery, and this experiment clearly demonstrates that it is also effective for recovery of oils in algae and microorganisms and the like.

Next, an algae culture solution (algae solution) that had been disrupted for 30 minutes with a cell wall or cell membrane disrupting device was supplied for hydrogen production. An anaerobic digestive bacteria solution used in sewage treatment plants was used as the hydrogen production seed bacteria. The digestive bacteria and algae solution were mixed in fixed proportions (digestive bacteria:algae solution=1:9, 5:5, 9:1), and the pH was adjusted to 5, and then, anaerobic digestion was carried out. The results are shown in FIG. 7B.

Comparative Example 5

As a control, an undisrupted algae culture solution (algae solution) was supplied for hydrogen production. In the same manner as Example 7, the digestive bacteria and algae solution were mixed in fixed proportions (digestive bacteria:algae solution=1:9, 5:5, 9:1), and the pH was adjusted to 5, and then, anaerobic digestion was carried out. The results are shown in FIG. 7B.

Figure 7B:
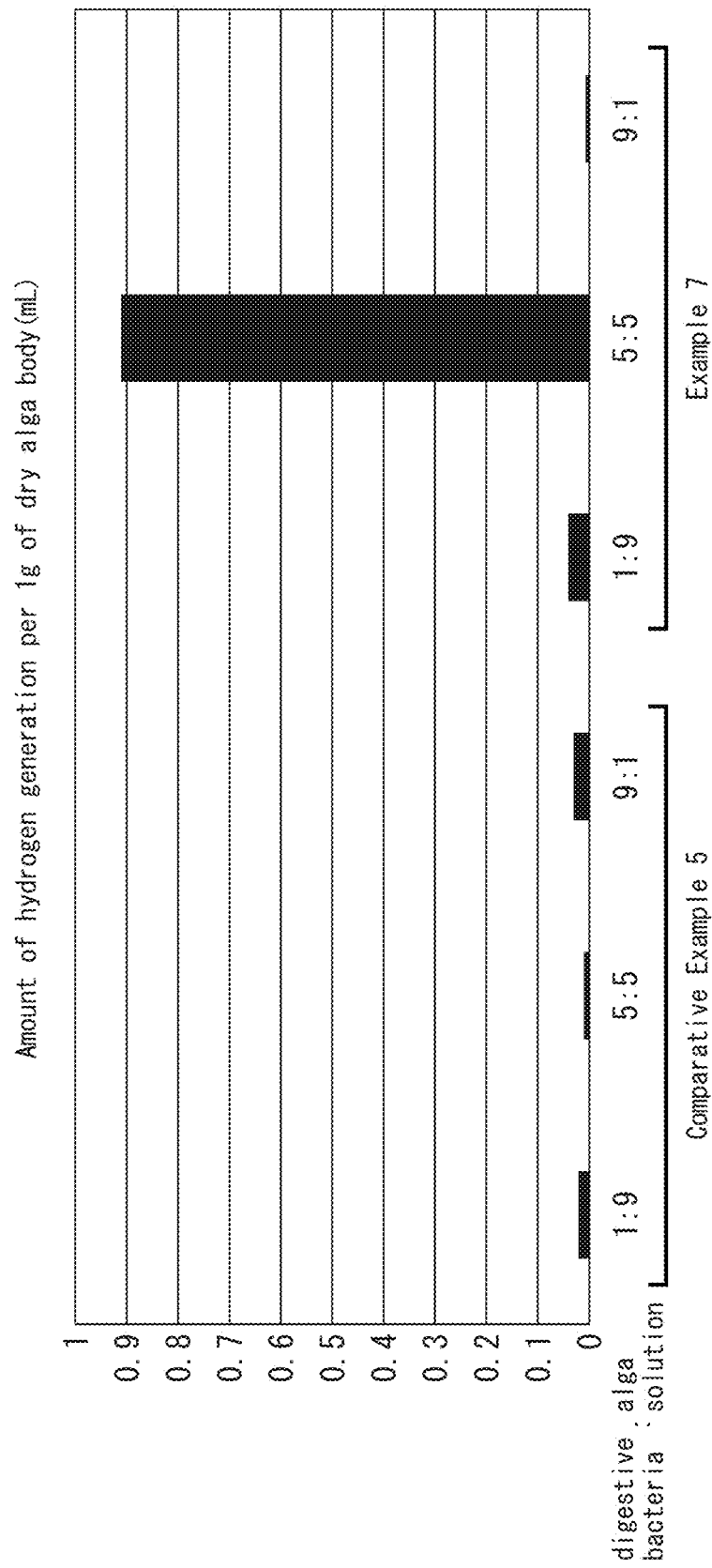
FIG. 7B is a bar graph showing the correlation between disrupted alga body and hydrogen generation (mL) per 1 g of dry alga body.

As seen from FIG. 7B, it was confirmed that virtually no hydrogen was generated in the system of Comparative Example 5 with any mixing ratio, whereas in Example 7, 0.9 mL of hydrogen gas was generated per 1 g of dry alga body when the disrupted algae solution and digested cells were mixed at 5:5. It was thus confirmed that the cell wall or cell membrane disrupting device can also contribute to generation of hydrogen as a by-product of methane fermentation.

It will be apparent to a person skilled in the art that the embodiments and examples described above may be modified in various ways that do not deviate from the basic principle of the present invention. It will also be apparent to a person skilled in the art that various modifications and changes to the present invention may be carried out without deviating from the gist and scope of the invention.

REFERENCE SIGNS LIST 100, 800 Cell wall or cell membrane disrupting device
105 Flow of target substance
110 Inverter
120 Motor
130, 230 Rotating shaft
140 Fixed disc
150, 250 Rotating disc
160, 260 Housing
170 Loading port
180 Discharge port
190 Pressure reducing means
295 Cloud
805 Pre-treatment storage tank
815 Land pump
825 Post-treatment storage tank

The invention claimed is:

1. A cell wall or cell membrane disrupting device comprising:
a plurality of fixed discs,
a plurality of rotating discs,
a rotating shaft for driving the rotating discs, the rotating discs spaced along the rotating shaft, wherein each two rotating discs located proximate one another along the rotating shaft form a pair,
at least one of a land pump and a submersible pump,
a housing arranged and configured to support the fixed discs and support the rotating shaft horizontally,
a loading port, and
a discharge port,
wherein the fixed discs have an approximately discoid shape,
wherein the rotating discs have an approximately discoid shape,
wherein at least one fixed disc and rotating disc are disposed facing each other in the housing, the center section of the fixed discs include a void that is larger than the outer diameter of the rotating shaft passing through the center section,
two or more fixed discs are arranged between each pair of rotating discs,
wherein the rotating disc and the fixed disc disposed facing each other are arranged and configured to generate a shearing force between the rotating disc and the fixed disc and to apply the shearing force to a target fluid having a water content of 89% or higher that has been loaded into the device, and
wherein the at least one of the land pump and the submersible pump are arranged and configured to reduce the pressure inside the cell wall or cell membrane disrupting device from −0.00001 MPa to −0.08 MPa.

2. The cell wall or cell membrane disrupting device according to claim 1, wherein the land pump is a one rotor screw pump.

3. The cell wall or cell membrane disrupting device according to claim 1, wherein the rotating disc rotates at a circumferential speed of 10 m/s or higher.

4. The cell wall or cell membrane disrupting device according to claim 1, which comprises two or more pairs of rotating discs.

5. The cell wall or cell membrane disrupting device according to claim 1, wherein the surfaces of at least one of the rotating disc and the fixed disc are mirror surfaces or rough surfaces.

6. The cell wall or cell membrane disrupting device according to claim 1, wherein the target substance to be loaded into the cell wall or cell membrane disrupting device contains at least one component selected from the group consisting of fungi, microorganisms, algae and plants.

7. The cell wall or cell membrane disrupting device according to claim 1, wherein the target substance to be loaded into the cell wall or cell membrane disrupting device is sludge.

8. A method of reducing sludge volume, comprising a step of treating sludge by the cell wall or cell membrane disrupting device according to claim 1.

9. A method of preparing fertilizer from sludge, comprising a step of treating sludge with the cell wall or cell membrane disrupting device according to claim 1, and a step of converting the treated sludge obtained from the step of treating sludge, to fertilizer.

10. A method of preparing a culture solution from sludge, comprising a step of treating sludge with the cell wall or cell membrane disrupting device according to claim 1, and a step of collecting the treated separated liquid obtained from the step of treating sludge, as a culture solution.

11. A deodorizing method comprising a step of treating sewage and/or sludge, or an odorous food, with the cell wall or cell membrane disrupting device according to claim 1.

12. A method of fermenting for obtaining biogas, the method comprising a step of treating sludge with the cell wall or cell membrane disrupting device according to claim 1, and a step of supplying the treated sludge and/or treated separated liquid obtained from the step of treating sludge, to a biogas fermenter.

13. A method for producing a food, beverage, drug, supplement or cosmetic, comprising a step of treating a target substance of at least one component selected from the group consisting of fungi, microorganisms, algae and plants, with the cell wall or cell membrane disrupting device according to claim 1.

14. A method for recovering an oil, the method comprising a step of treating a target substance containing at least one kind of oil component selected from the group consisting of fungi, microorganisms, algae and plants, with the cell wall or cell membrane disrupting device according to claim 1.

15. The cell wall or cell membrane disrupting device according to claim 1, which comprises a device arranged and configured to heat at 30° C. or higher and at lower than 50° C.

16. The cell wall or cell membrane disrupting device according to claim 1, wherein the gaps between each of the discs are continuously, stepwise or partially increased from the loading port end toward the discharge port end.

17. The cell wall or cell membrane disrupting device according to claim 1, wherein the gap between the fixed disc and rotating disc disposed facing each other is 5 mm to 30 mm.

* * * * *